(12) United States Patent
Nallakrishnan et al.

(10) Patent No.: US 10,004,642 B1
(45) Date of Patent: Jun. 26, 2018

(54) APPARATUS AND METHOD FOR CORNEAL MARKING

(71) Applicant: ART, LIMITED, Grand Cayman (KY)

(72) Inventors: Ravi Nallakrishnan, Westmont, IL (US); Takayuki Akahoshi, Tokyo (JP)

(73) Assignee: ART, LIMITED (KY)

( * ) Notice: Subject to any disclaimer, the term of this patent is extended or adjusted under 35 U.S.C. 154(b) by 344 days.

(21) Appl. No.: 13/867,934

(22) Filed: Apr. 22, 2013

Related U.S. Application Data

(60) Provisional application No. 61/794,011, filed on Mar. 15, 2013, provisional application No. 61/755,945, filed on Jan. 23, 2013, provisional application No. 61/636,668, filed on Apr. 22, 2012.

(51) Int. Cl.
*A61F 9/013* (2006.01)

(52) U.S. Cl.
CPC .................. *A61F 9/0136* (2013.01)

(58) Field of Classification Search
CPC .... A61F 9/0008; A61F 9/0017; A61F 9/0026; A61F 9/013; A61F 9/0133; A61F 9/0136; A61F 2009/0035; A61F 2009/0043; A61F 2009/0052; G01C 9/06
See application file for complete search history.

(56) References Cited

U.S. PATENT DOCUMENTS

| | | | | |
|---|---|---|---|---|
| 4,506,450 A | * | 3/1985 | Fleming | G01C 9/06 33/348 |
| 5,308,355 A | * | 5/1994 | Dybbs | A61F 9/0133 600/452 |
| 6,217,596 B1 | * | 4/2001 | Farah | A61F 9/0136 606/166 |
| 2004/0167540 A1 | * | 8/2004 | Gerten | A61F 9/0136 606/116 |
| 2004/0194329 A1 | * | 10/2004 | Drahos | G01C 9/06 33/366.11 |
| 2014/0330297 A1 | * | 11/2014 | Akahoshi | A61F 9/0136 606/166 |

FOREIGN PATENT DOCUMENTS

WO    WO 2011047076 A1 * 4/2011 ............. A61B 3/152

\* cited by examiner

*Primary Examiner* — Ryan J Severson
*Assistant Examiner* — Christian Knauss
(74) *Attorney, Agent, or Firm* — Wood, Phillips, Katz, Clark & Mortimer

(57) ABSTRACT

A corneal marking system, and methods for its use, has a tilt-detecting device attached to a corneal marker, adapted to produce a signal when the corneal marker is in a horizontal position. Use of measurement devices may be coordinated between the marker and a level-measuring device positioned on a patient's head. Devices capable of measuring one, two or three axes are used and processors are provided to evaluate the data produced by the devices and provide a physician with a signal that the positions of the patient's head and the marker are such that an accurate marking procedure can be performed.

10 Claims, 19 Drawing Sheets

Fig. 3
Prior Art
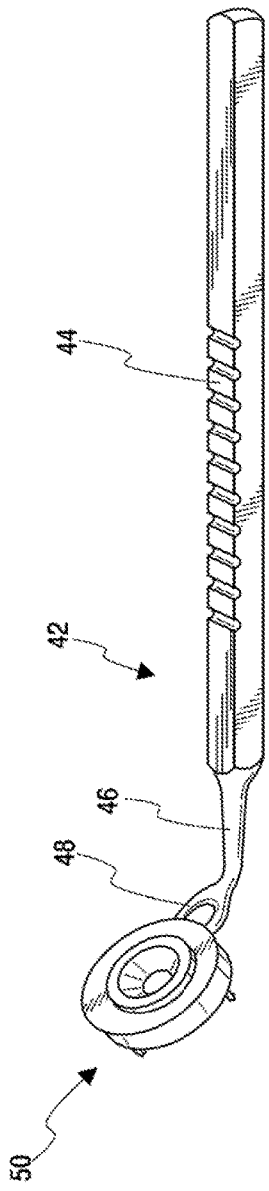
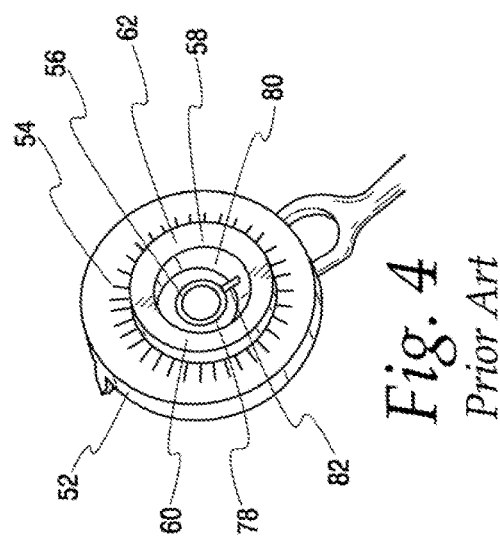
Fig. 4
Prior Art
Fig. 5
Prior Art

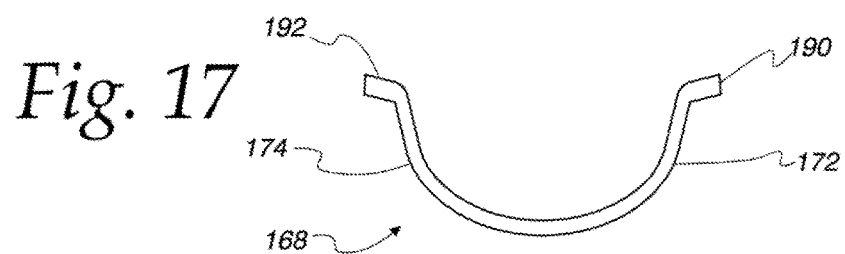
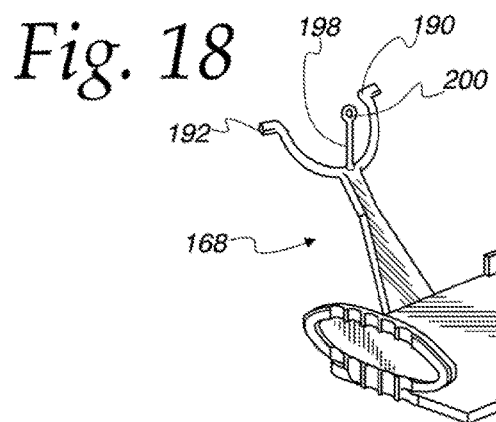
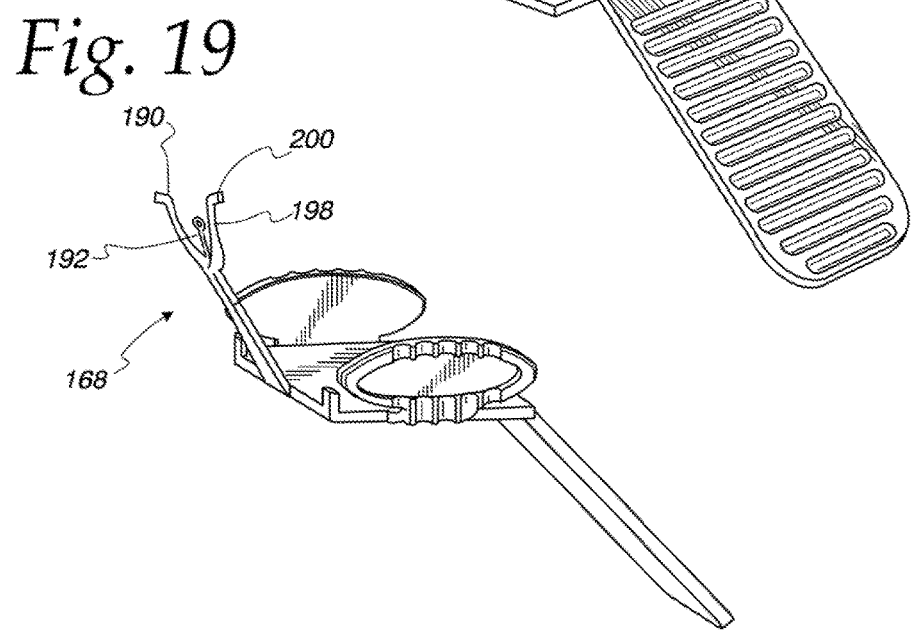

APPARATUS AND METHOD FOR CORNEAL MARKING

This application claims priority from U.S. provisional patent application Ser. No. 61/794,011, filed Mar. 15, 2013, entitled "Apparatus and Method for Corneal Marking". This application further claims priority from U.S. provisional patent application Ser. No. 61/755,945, filed Jan. 23, 2013 and entitled "Apparatus and Method for Corneal Marking". This application further claims priority from U.S. provisional patent application Ser. No. 61/636,668, filed 22 Apr. 2012, and entitled "Apparatus and Method for Corneal Marking". This application is a continuation-in-part of U.S. non-provisional patent application Ser. No. 12/581,665, filed Oct. 19, 2009, and entitled: "Apparatus and Method for Corneal Marking". All of the above-referenced prior-filed applications are incorporated herein by reference in their entireties.

BACKGROUND OF THE INVENTION

The present invention relates generally to instruments used in ophthalmic surgery and, more particularly, to instruments used to mark the cornea prior to the implantation and alignment of an intraocular lens (IOL).

Replacement of a cataract with an artificial IOL is now a well-accepted surgical procedure. Typically, during such a procedure the diseased lens is removed from the capsular bag by phacoemulsification and a soft, plastic IOL is folded, inserted into the capsular bag and allowed to unfold to act as a replacement lens.

Early implantable IOLs did not afford any correction for corneal astigmatism and a patient suffering from such a condition would still have to wear glasses even after the cataract was removed and a new lens inserted in its place.

Alcon Industries has developed its AcrySof® toric IOL which combines the flexibility of an implantable IOL with the astigmatic corrections available in typical glass or plastic eyeglass lenses. In order to use a toric IOL effectively, the lens must be rotated in the capsular bag to align the lens with a pre-calculated optimal axis, typically the steepest curvature of the cornea. To do so, a keratometer is used to measure the curve of the patient's cornea and to determine the steep axis of the cornea. When the toric IOL is implanted, a pair of reference marks on the toric IOL are aligned with the steep axis to provide the desired vision correction. As used herein, the term "keratometer" also refers to a corneal measuring device that includes means for placing marks on the cornea.

It is important to have an accurate measurement of the corneal curvature and equally important to find a method for identifying the steep axis during surgery so the IOL can be aligned properly.

The present invention relates to instruments which are used to mark the cornea of the patient to identify pre-phacoemulsification reference points to determine the orientation of the steep axis of the cornea so that after phacoemulsification the IOL can be rotated to align it properly with the steep axis.

Prior to phacoemulsification the patient's eye is examined with a keratometer and a toric IOL calculator is then used to determine the angle of the steepest, or "steep" axis along which the astigmatism is most pronounced and with which the lens needs to be aligned. The angle is then recorded so the IOL can be accurately aligned when inserted into the eye.

In preparation for surgery, the patient is seated in an upright position and a corneal marker is used to mark the 3-, 6- and 9 o'clock positions on the cornea, with the 3- and 9 o'clock positions corresponding to the corners of the eye and the 6 o'clock position corresponding to the bottom of the eye. These will be the reference points for later marking of the steep axis.

The corneal marker includes a series of tabs formed on the front surface of a circular ring, placed at 90° intervals. The rear of the ring includes a number of marking tabs intended to come into contact with the cornea. After the marking tabs are coated with dye, one marking tab is aligned with the limbus of the eye and the instrument is then pressed against the cornea to leave marks corresponding to the 3-, 6- and 9 o'clock positions.

A second corneal marker, made specifically for marking the steep axis has a pair of axis marking tabs on the rear and a scale on the front, marked in degrees. Some corneal markers may also include a rotating ring, commonly mounted within a fixed ring, with the fixed ring used to mark the reference points and a rotating ring used to mark the steep axis. The rotating ring has a pair of axis marking tabs formed on its rear surface.

When the patient is ready for surgery, one of the corneal markers described above is used to mark the steep axis. If the second corneal marker has a fixed set of tabs, the scale on the front of the marker is read to correspond with the steep axis by aligning the axis reading with the reference points already present on the cornea. If a corneal marker with a rotating ring is used, the marker is aligned with the reference points and the ring is rotated until the steep axis setting is reached and the marker is allowed to come into contact with the cornea to press the axis tabs, aligned with the angle marking on the marker, against the cornea. The axis tabs make a pair of marks on the cornea, and it is this second set of reference marks that identifies the axis with which the IOL is aligned when it is inserted so that the stigmatic correction of the IOL is maximized.

The corneal marker will work more accurately to make the reference marks if it is held in a horizontal position when the patient is sitting up. To position the marker, the user hold it to align the handle in a generally horizontal orientation. The marker will work most accurately if it is held in a horizontal position when the patient's eyes are also aligned horizontally, as in when the patient is sitting up. To position the marker, the user holds it in as horizontal an orientation as possible, aligns the marker with the patient's eye and then presses it against the eye so that the dye-coated axis tabs make the desired reference marks on the cornea. It is important for the corneal marker to be held as nearly level as possible during the marking process.

Examples of markers and tilt detectors are found in the prior art.

U.S. Pat. No. 6,217,596 (Farah) teaches and describes a corneal surface and pupillary cardinal axes marker having an inclinometer mounted on the frame.

U.S. Patent Application Publication 2008/0228210 (Davis) describes prior art markers having level gauges or plumb bobs to indicate when the marker handle is being held in the horizontal position.

U.S. Pat. No. 4,739,761 teaches and describes a cornea marker that employs a rotating marker wheel to allow the cornea to be marked at selected locations.

It is an object of the present invention to provide instruments useful for marking the cornea for the insertion and alignment of a multifocal IOL while allowing the surgeon to double check the location of the corneal steep axis prior to insertion of the lens.

It is a further object of the present invention to provide a convenient and accurate way in which to assure that the corneal marker and the patient's eye are properly aligned to make an accurate measurement.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

These and further objects of the present invention will become more apparent upon considering the accompanying drawings in which:

FIG. 3 is a perspective view of a prior art corneal axis marker;

FIG. 4 is a top detail view of the marking end of the marker in FIG. 3;

FIG. 5 is a bottom detail view of the marker in FIG. 3;

FIG. 17 is a detailed view of the marker arms of the device of FIG. 13;

FIG. 18 is a rear perspective view of another embodiment of the device of FIG. 13;

FIG. 19 is a lateral perspective view of the device of FIG. 18;

DETAILED DESCRIPTION OF THE DRAWINGS

Figure 1:
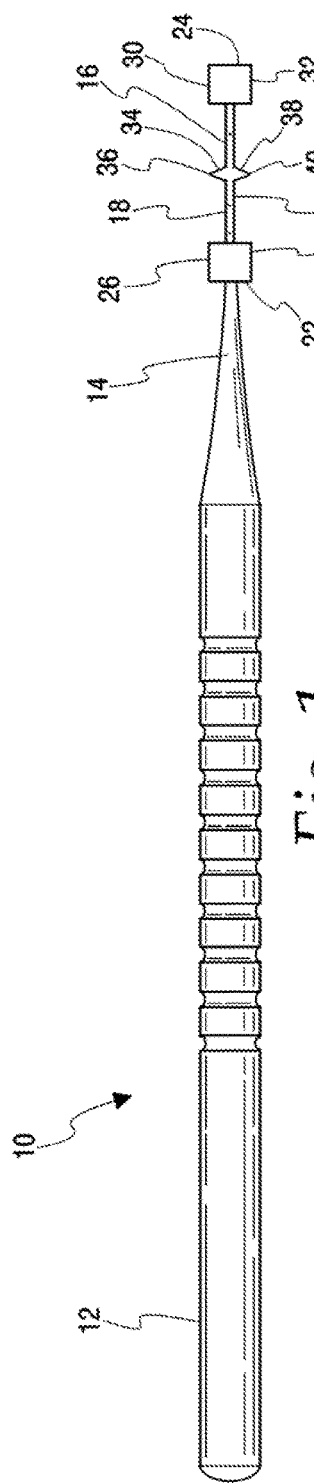
FIG. 1 is a perspective view of a prior art corneal reference marker.
Figure 2:
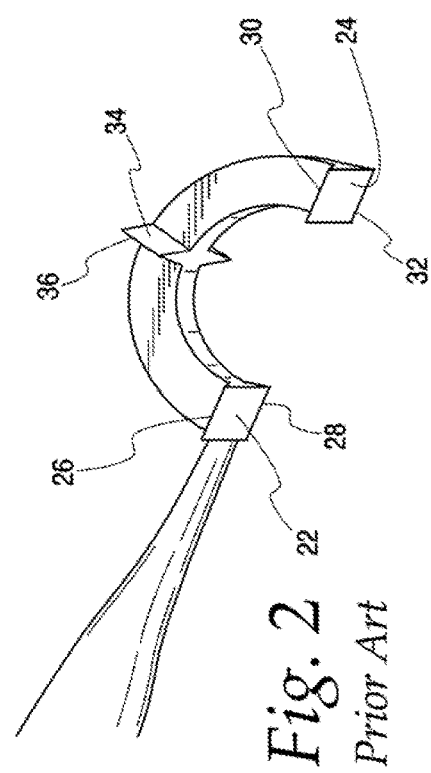
FIG. 2 is a detail of the marking end of the marker shown in FIG. 1.

Referring now to FIG. 1, the numeral 10 identifies a prior art reference toric marker. Reference marker 10 has a handle 12 tapering at one end to form a throat 14 to which a marker blade 16 is integrally, fixedly and non-rotatably attached. As seen in FIG. 1, blade 16 has an upper surface 18 and a lower surface 20 and is preferably formed as a semicircular flat segment. As best seen in FIG. 2, blade 16 has first and second marking tabs 22, 24 formed diametrically opposite one another and formed integrally with blade 18. Tab 22 has an upper marking edge 26 and a lower marking edge 28 while tab 24 has an upper marking edge 30 and a lower marking edge 32.

A third marking tab 34 is formed integral with upper surface 18 and midway along blade 16 between first and second marking tabs 22, 24. Tab 34 has an upper marking edge 36. A fourth marking tab 38 having a lower marking edge 40 extends from lower surface 20 opposite third marking tab 34.

While the marking tabs 22, 24, 34 and 38 are shown in FIGS. 1 and 2 as elongated "knife edges" other shapes can be used for the marking tabs. For example, raised hemispherical dots can also be used. The shape of the marking tab can determine the shape and size of the mark left on the cornea.

Referring now to FIG. 3, the numeral 42 identifies an axis marker having a handle 44 tapering to a throat portion 46 to which a mounting fork 48 is integrally attached at a preselected and nonadjustable angle.

Attached to fork 48 is a combined gauge and keratometer assembly 50. As best seen in FIGS. 4 and 5, assembly 50 comprises a toroidal gauge ring 52 having an upper surface 54 onto which a scale marked off in degrees from zero to 180 is engraved. Ring 52 is attached to fork 48 such that a 90° marking on the scale is positioned at fork 48. Ring 52 does not rotate with respect to fork 48.

Gauge ring 52 has a central circular aperture 56 formed therethrough. An inner toroidal marker ring 58 is rotatably fitted to gauge ring 52 through aperture 56. Ring 58 has a first right circular segment 60 held rotatably within the gauge ring 52 with first segment 60 extending above upper gauge ring surface 54. A reference mark 62 is engraved on ring 58.

Referring now to FIG. 5, pair of locating tabs 70, 72 are formed on the lower surface of gauge ring 52 preferably to coincide with the 90/90° marks on top surface 54 of ring 52. Also as seen in FIG. 5, a pair of marking tabs 74, 76 are formed on the lowermost surface of third marker ring segment 64. As can be appreciated, marking edges 74, 76 will rotate as marker ring 58 is rotated.

A keratometer ring 78 is attached to inner wall 80 of marker ring 58 by ring shaft 82. When axis marker 42 is placed on a patient's cornea, light from the operating microscope is directed through keratometer ring 78 and will highlight the general shape of any astigmatism in the cornea. This is not intended as a precise identification of the position of the steep axis of the cornea, but is intended to provide a backup indicator to confirm to the surgeon that the previously obtained keratometer readings were correct in identifying the steep axis.

In use, marking tabs 74, 76 are coated with a suitable dye and marker ring 58 is rotated to bring reference mark 62 in alignment with the scale scribed on surface 54 to coincide with the angle of the previously-measured steep axis. Non-rotating markers 70, 72 are then coated with a suitable dye. The instrument is then placed on the eye to bring one of the non-rotating tabs 70, 72 at the corner of the eye such that tabs 74, 76 are in alignment with the steep axis. Tabs 74, 76 are then pressed against the cornea to leave a pair of marks that allow the surgeon to align the IOL along the steep axis after insertion.

As shown in FIGS. 4 and 5, ring 78 is formed with a single ring, but multiple concentric rings can also be used to provide differing light patterns and effects as desired.

Figure 6:
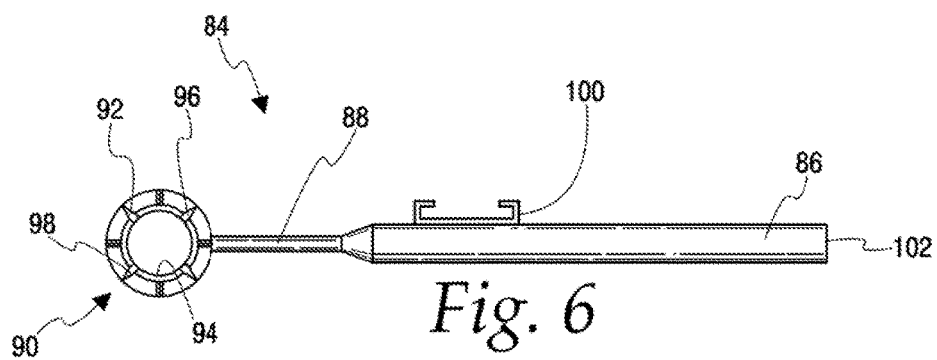
FIG. 6 is a lateral view of a marker embodying certain principles of the present invention.

Referring now to FIG. 6, the numeral 84 identifies generally a corneal marker having a handle 86 from which extends a throat 88. A keratometer assembly 90 is mounted to the distal end of throat 88 and includes a fixed marked scale 92 and an inner rotating ring 94 to which indexing markers 96, 98 are attached.

It is to be understood that keratometer assembly 90 is assembled and functions generally in accordance with the foregoing descriptions of keratometer assemblies having rotating index rings and having marking tabs formed on the rotating and non-rotating portions of the assembly. In the view shown in FIG. 6, the marking tabs are on the reverse side of keratometer assembly 90 and are not visible.

A tilt detector mount 100 is attached to handle 86 intermediate throat 88 and handle end 102.

Figure 7:
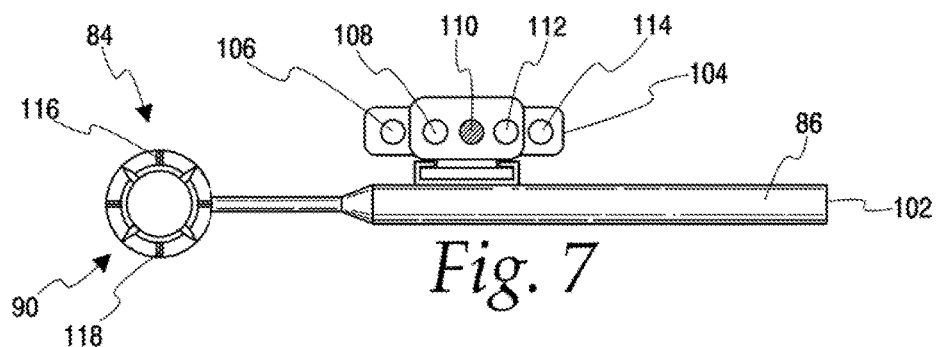
FIG. 7 is a lateral view of the marker of FIG. 6 with a tilt detector secured thereto.

Referring now to FIG. 7, the numeral 104 identifies a tilt detector of the type having a series of light emitting diodes (LEDs) 106, 108, 110, 112 and 114. Such a device is marketed by Velbon and is identified as an action level.

As tilt detector 104 is inclined with respect to the horizontal, various of the LEDs 106, 108, 110, 112, and 114 will sequentially light up to identify the orientation of tilt detector 104 and thereby handle 86. For example, if handle 86 is inclined to the right with keratometer assembly 90 being higher than handle end 102, LEDs 106, 108 will be illuminated. In similar fashion, if marker 84 is tilted such that keratometer assembly 90 is lower than handle end 102, LEDs 112, 114 will be illuminated. When center LED 110 is illuminated, handle 86 is in a horizontal position and reference marks 116, 118 are aligned vertically.

Tilt detector 104 is of the type that can also emit a characteristic sound when it is level and LED 110 is lit, or to warn when it is not level. Such detectors can thus provide both visual and auditory signals to indicate various stages of alignment.

Use of corneal marker 84 is enhanced when the patient's head is positioned so that the patient's eyes are horizontally level.

Figure 8:
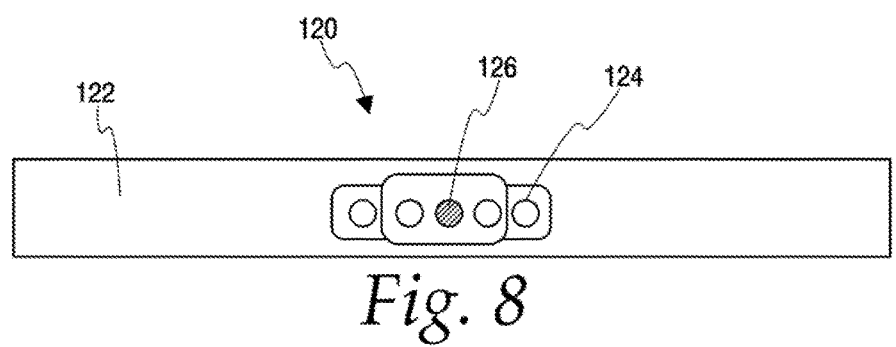
FIG. 8 is a plan view of a headband having a tilt detector.

Referring now to FIG. 8, the numeral 120 identifies a headband assembly comprising a headband 122 to which a tilt detector 124 is attached. In this embodiment, the construction, function and operation of tilt detector 124 is similar to that of device 104. When headband 120 is held in a horizontal position, central LED 126 will be illuminated. In addition, tilt detector 124 can also emit an audible sound signal to indicate that it is in the level position. The remaining LEDs on tilt detector 124 serve as a visual indicator to the user that headband 122 is not level and indicates the direction in which headband 122 must be inclined to be level.

In use, headband 122 is placed around the patient's forehead as the patient is in a seated position. The patient's head is moved to produce a signal that the headband and, thereby, the patient's head are in a position to horizontally level the patient's eyes.

Corneal marker 84 is placed near the eye to be marked and handle 86 is inclined until a "level" signal is produced by tilt detector 104. When both tilt detectors 104, 124 produce level signals then keratometer assembly 90 is correctly oriented to mark the patient's eye.

Figure 9:
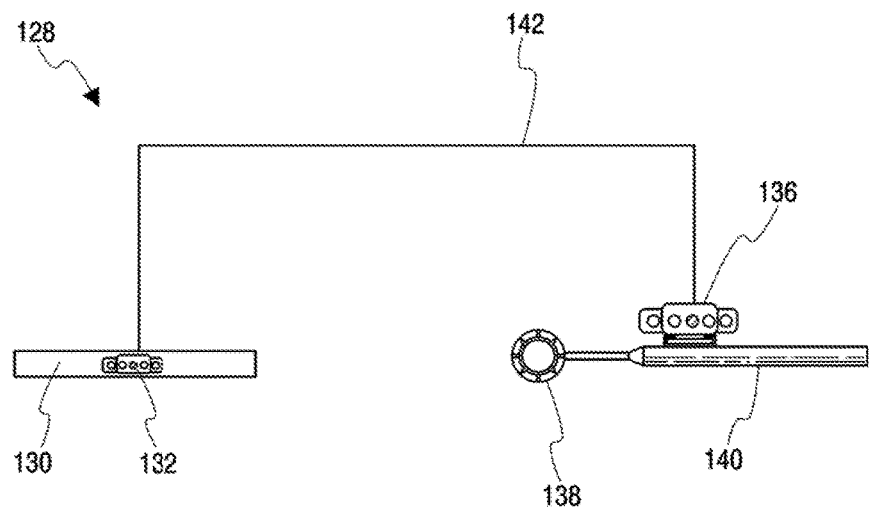
FIG. 9 is a view of the aforesaid marker and headband being used in tandem.

Referring to FIG. 9, an alternate embodiment of the present invention is illustrated. Leveling assembly 128 has a headband 130 to which a tilt detector 132 is affixed. A corneal marker 134 is also provided having a tilt detector 136 thereon and operating such that keratometer assembly 138 may be leveled by manipulating handle 140.

A communication pathway 142 extends between devices 132 and 136. Pathway 142 may consist of an electrically conductive wire and may also indicate a pathway created wirelessly by broadcast and receiving circuits provided in tilt detectors 132, 136.

Tilt detectors 132, 136 are adapted to communicate to each other and to indicate the degree to which each is inclined with respect to a selected reference. In the most common case, the selected reference will be the horizontal direction. Using the arrangement of FIG. 9, it is not necessary to have headband 130 aligned to a horizontal position and to have marker 134 aligned to a horizontal position. Instead, tilt detectors 132, 136 are adapted to emit either a visual or audible signal when both are oriented alike. Thus, if headband 130 is aligned to an inclination of 5° from true horizontal, a confirming signal will be broadcast when corneal marker 134 is also inclined to 5° from true horizontal. In this manner, headband 130 and corneal marker 134 can be properly oriented without requiring separate leveling observations on independently operating tilt detectors and without requiring both to be horizontally level.

Figure 10:
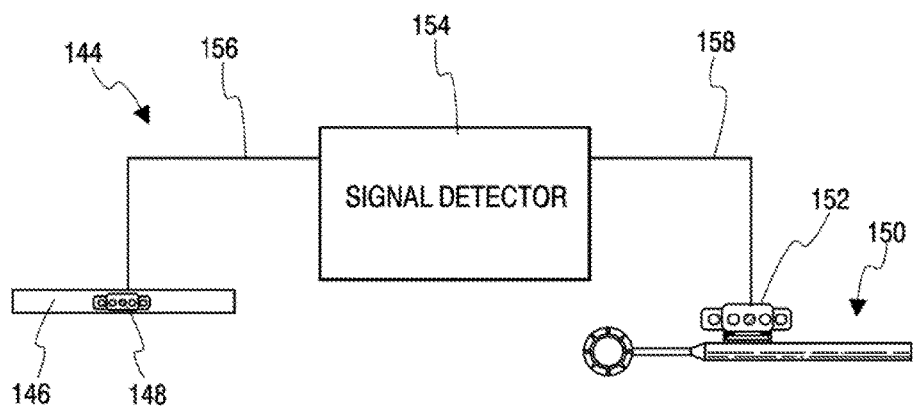
FIG. 10 is another embodiment of the arrangement of FIG. 9.

Referring now to FIG. 10, an alternate arrangement of the leveling assembly of FIG. 9 is shown. Leveling assembly 144 is shown having headband 146 to which a tilt detector 148 is attached, and a corneal marker 115 to which a tilt detector 152 is attached. A signal detector 154 is provided and is connected such that a first communication passageway 156 extends from tilt detector 148 to signal detector 154 and a second communication pathway 158 extends from tilt detector 152 to signal detector 154.

Using such an arrangement, signal detector 154 can audibly, visually, or a combination thereof, indicate when tilt detectors 148, 152 are held in identical orientations with respect to a selected reference. As described above, communication passageway 156, 158 can be wired or wireless.

As seen in FIGS. 6 and 7, the tilt detector associated with each of both described corneal markers may be removed to allow the corneal marker to be sterilized. The tilt detector can be inserted from either side of the mount so that the corneal marker can be aligned to be used with both left and right eyes. Alternatively, a set of LEDs can be positioned on both sides of the tilt detector so it can be read from front or rear.

It is also contemplated that a tilt detector constructed to withstand the sterilization process can be mounted in the handle itself.

If it is desired to keep patient distractions to a minimum when using the audible signal to verify alignment the signal can be set to broadcast to a set of headphones or an earpiece. The readings of both the corneal marker and the headband can be stored in a computer to make a full record of the patient's procedure for later review.

In use, the patient is first fitted with a headband constructed in accordance with the foregoing. Where there is a preset inclination, the patient is assisted to reach a head position where the preset is met as indicated by the signal generated by the tilt detector mounted on the headband. Next, a corneal marker, constructed as set forth herein, is selected, having a tilt detector with a preset inclination matching that of the headband. The corneal marker is adjusted to produce a signal confirming that the headband and the corneal marker are both aligned to the same preset inclination and the marking of the cornea is then carried out.

Where there is no preset inclination, the headband tilt detector and the corneal marker tilt detector are set to emit a signal when both are aligned to the same inclination. Once this signal is produced corneal marking can proceed. In this manner, even if the patient's head moves, an accurate reading will still be obtainable.

Figure 11:
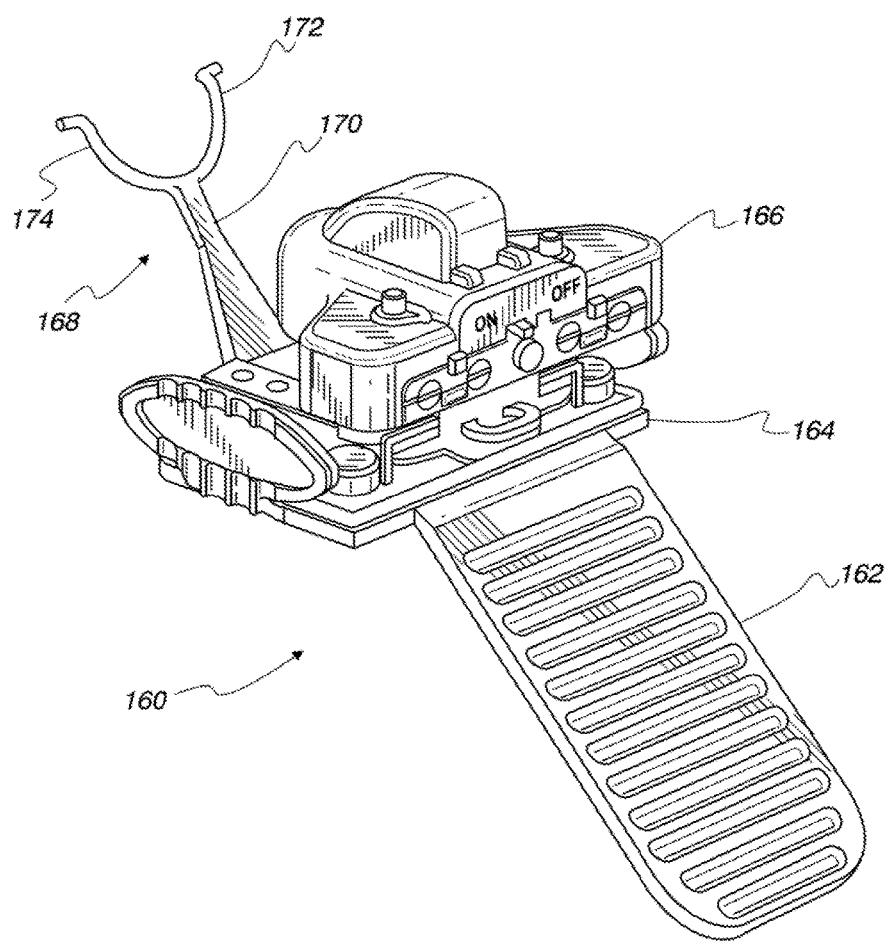
FIG. 11 is a rear perspective view of a corneal marker embodying certain principles of the present invention.
Figure 14:
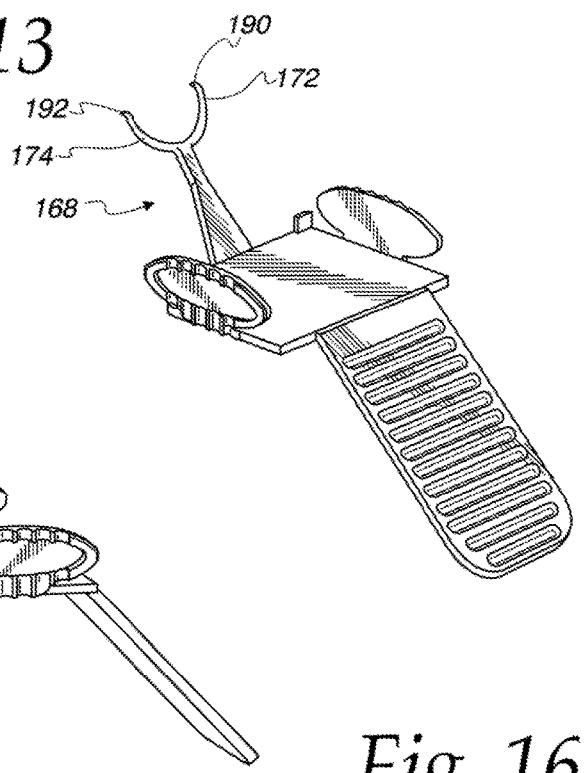
FIG. 14 is a rear perspective view of the device of FIG. 13.

Referring now to FIG. 11, the numeral 160 identifies generally another embodiment of a corneal marker, one having a handle 162 to which a mounting platform 164 is attached. Platform 164 provides a site for the removable attachment of an electronic level 166. As seen in FIG. 14, a keratometer 168 is attached to the front edge 164A of platform 164 and has a body 170 and a pair of marking arms 172, 174 positioned at the end of body 170.

Figure 12:
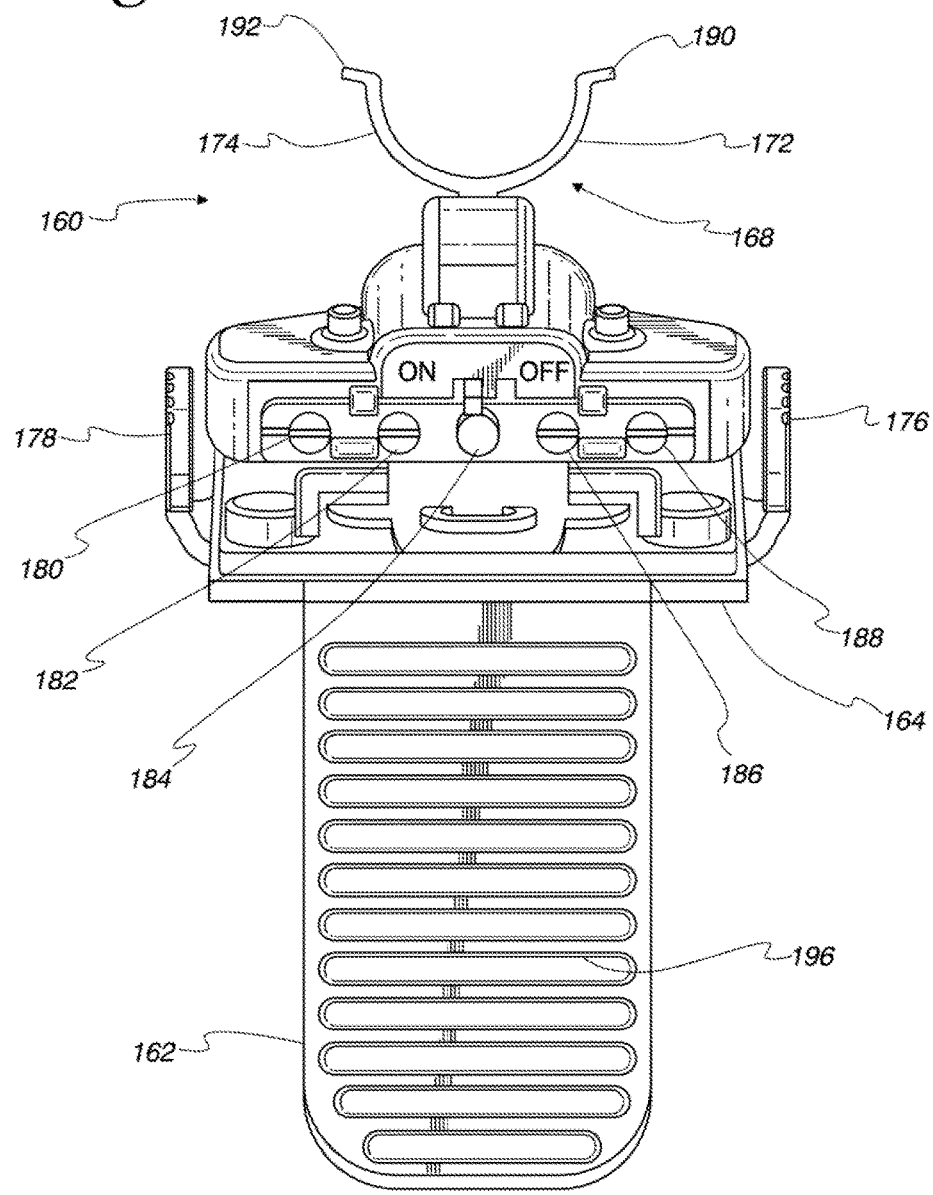
FIG. 12 is a rear view of the device of FIG. 11.

Referring now to FIG. 12, platform 164 has a pair of opposed side panels 176, 178, acting as guards for electronic level 166. Preferably, panels 176, 178 are formed integrally with platform 164.

FIG. 12 also shows that electronic level 166 has a series of indicator lights, preferably light emitting diodes (LEDs) 180, 182, 184, 186 and 188. One form of such a device is marketed by Velbon and is identified as an "action level". When electronic level 166 is turned on and corneal marker 160 is moved, the number and color of LEDs illuminated act as a guide to determining if electronic level 166 and, thereby, corneal marker 160 are level, or aligned horizontally. As an example, if lights 180, 182 are lit, corneal marker 160 is tilted too far to the left. If lights 186, 188 are lit, corneal marker 160 is tilted too far to the right. When light 184 (or, if desired, all lights 180-188) are lit, corneal marker 160 is level.

Figure 13:
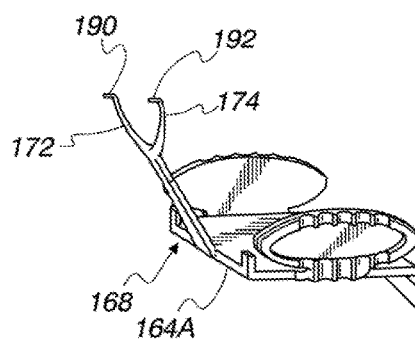
FIG. 13 is a perspective view of the device of FIG. 6 with the level detecting device removed.

As seen in FIGS. 12, 13 and 14, showing corneal marker 160 with electronic level 166 removed, keratometer 168 has mounted thereto a pair of curved marking arms 172, 174. Arm 172 terminates at a marking blade 190 while arm 174 terminates at a marking blade 192. Marking blades 190, 192 are used as described generally above to place reference marks on the eye prior to the insertion of an IOL.

Figure 15:
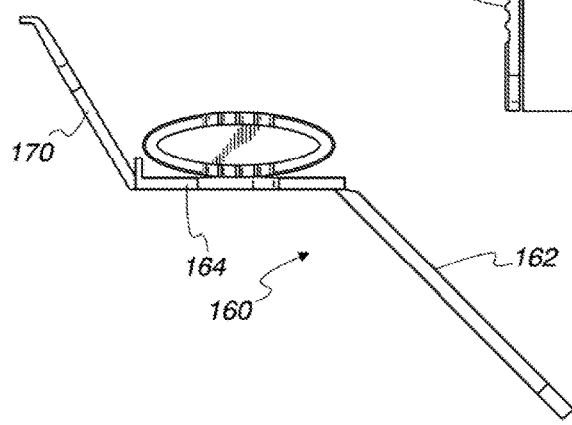
FIG. 15 is a lateral view of the device of FIG. 13.
Figure 20:
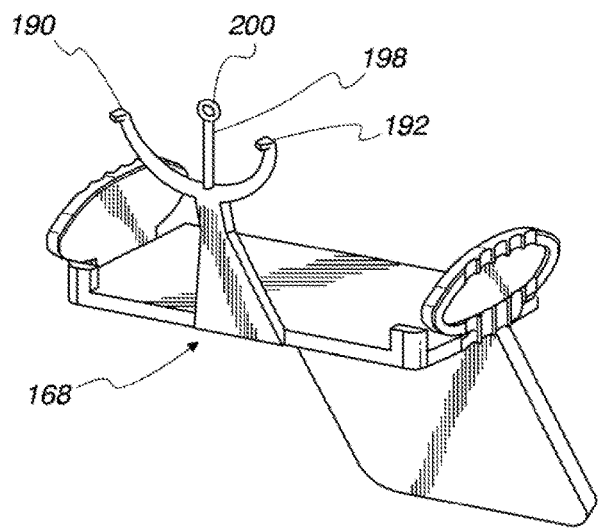
FIG. 20 is a front perspective view of the device of FIG. 18.
Figure 21:
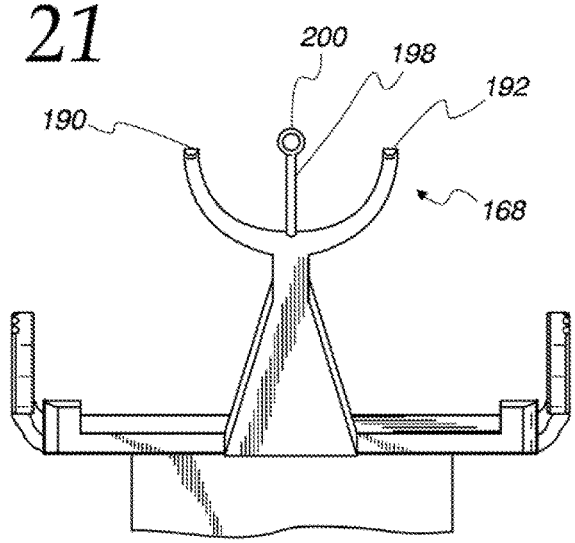
FIG. 21 is a front view of the device in FIG. 18.
Figure 22:
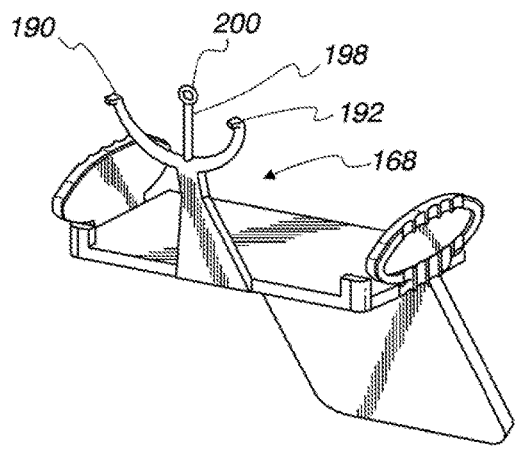
FIG. 22 is front perspective view of the device in FIG. 18.

Referring now to FIG. 15, a lateral view of corneal marker 160 is shown with electronic level 166 removed. As seen in FIG. 14, handle 162 is attached at an angle to platform 164 as is corneal marker handle 170.

Figure 16:
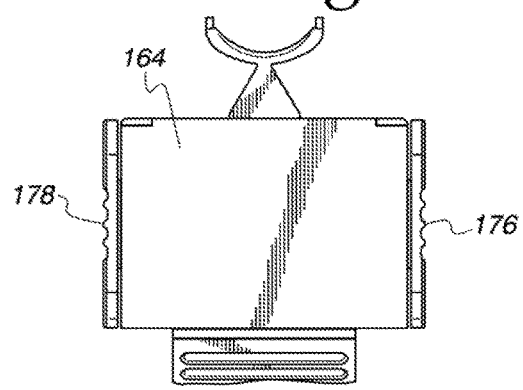
FIG. 16 is a partial top view of the device of FIG. 13.

Referring to FIG. 16, a top view of the device shown in FIG. 15 illustrates the flat planar construction of platform 164 and the positioning of side panels 176 and 178.

Referring now to FIG. 17, an enlarged detail of keratometer 168 is shown wherein it can be seen that marking blade 190 is set at an angle A to arm 172 and marking blade 192 is set at a similar angle A to arm 174. In use, dye is applied to the ends of blades 190, 192 which are then pressed against the cornea to create the alignment marks used during surgery.

Referring now to FIGS. 18, 19, 20, 21 and 22 a second embodiment of a mounted keratometer is shown, again with electronic level 166 removed. In this embodiment, keratometer 168 has a guide post 198 terminating in a guide ring 200 attached to handle 170 intermediate arms 172, 174.

Figure 23:
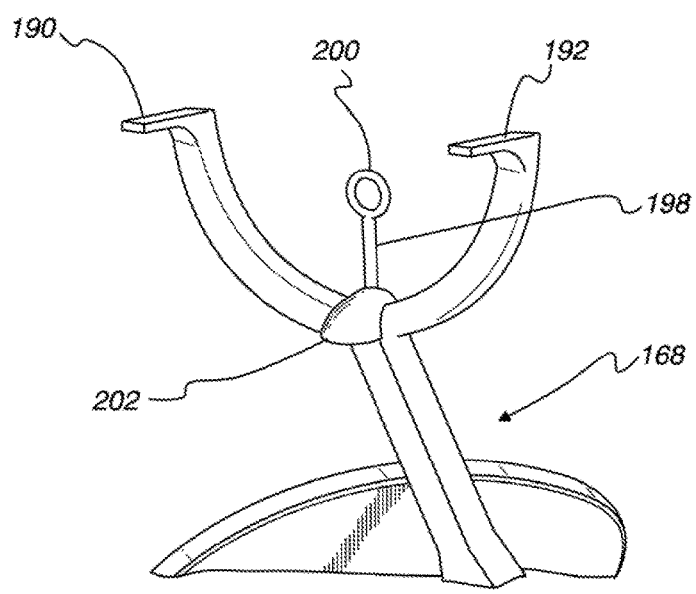
FIG. 23 is a detail view of FIG. 22.

As seen in FIG. 23, yet another variation of keratometer 168 is shown having guide post 198, guide ring 200, marking blades 190 and 192, and a third marking blade 202 positioned intermediate arms 172, 174 at handle 170. This arrangement gives the surgeon an option to provide a third reference mark on the cornea by inking blades 190, 192 and 202.

Figure 24:
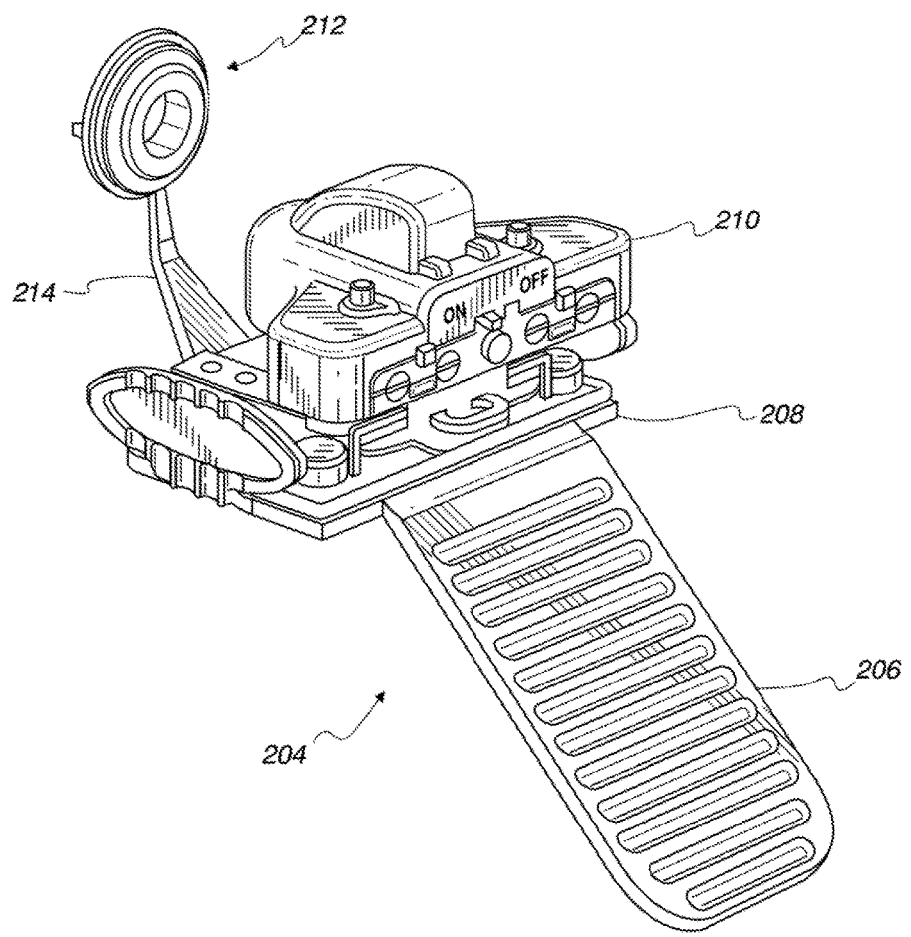
FIG. 24 is a rear perspective view of another embodiment of the present invention using a rotating-ring keratometer.

Referring now to FIG. 24, the number 204 identifies another embodiment of a corneal marker, having a handle 206, a platform 208, and an electronic level 210, all of which are arranged to function as described above with respect to handle 162, platform 164 and electronic level 166. A rotating keratometer 212 is mounted to a stalk 214 attached to the front portion of platform 208.

Figure 25:
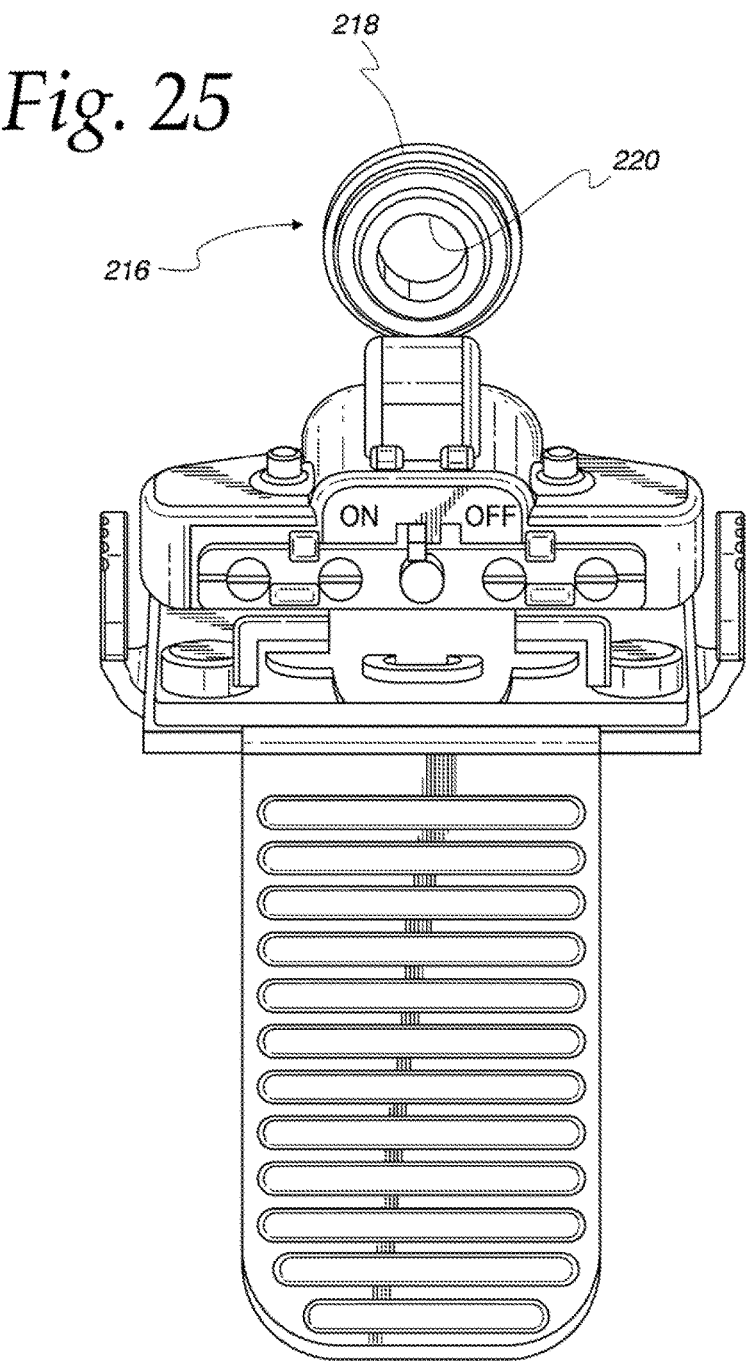
FIG. 25 is a rear view of the device of FIG. 23.

Referring now to FIG. 25, keratometer 212 is shown having a head assembly 216 comprising a first fixed ring 218 to which a second, marking ring 220 is rotatably mounted. Marking ring 220 can thus be rotated with respect to fixed ring 218. The rings have scales marked off in degrees of rotation scribed thereon as is conventionally done to allow the rings to be offset a measured rotation with respect to each other.

Figure 26:
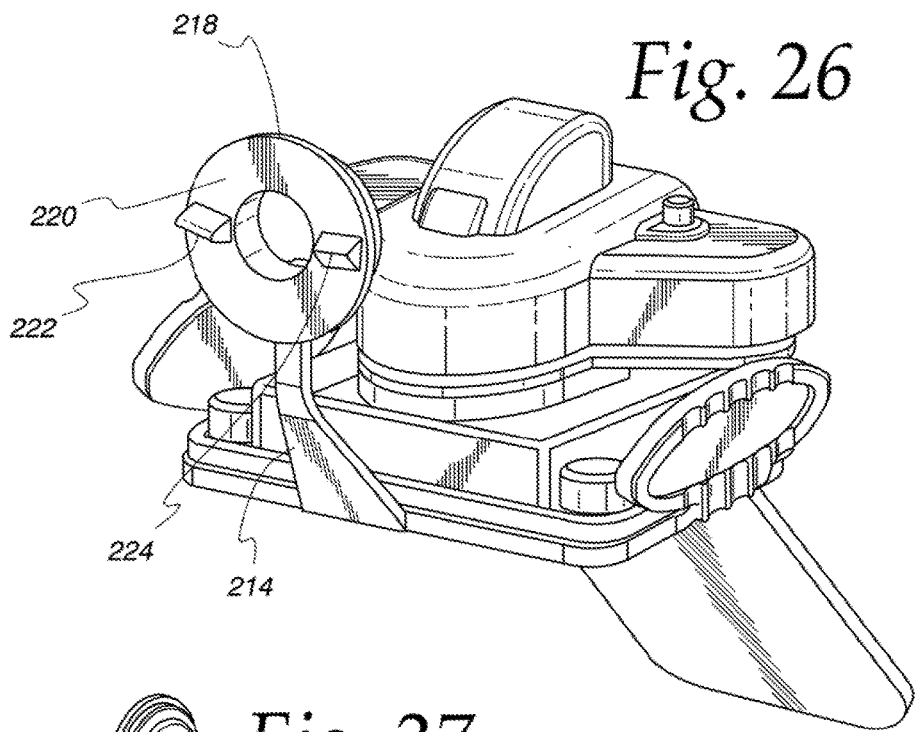
FIG. 26 is a front perspective view of the device of FIG. 23.

Referring to FIG. 26, rotatable ring 220 is shown having a pair of marking blades 222, 224 attached diametrically opposed to one another on the rear face 226 of rotating ring 220.

Figure 27:
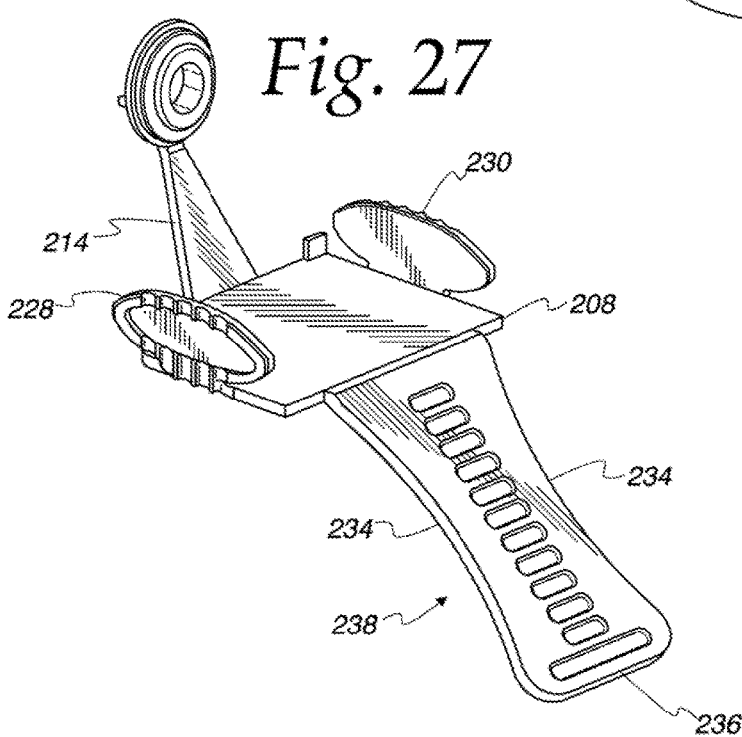
FIG. 27 is a left rear perspective view of the device of FIG. 23 with the level indicating device removed.
Figure 28:
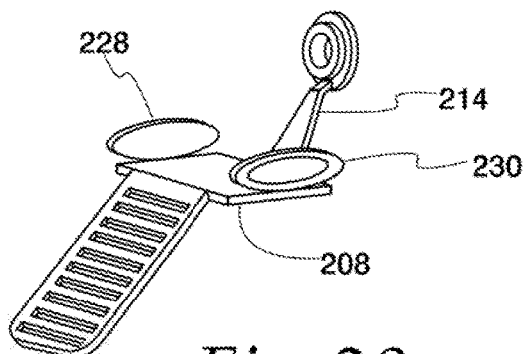
FIG. 28 is a right rear perspective view of the device of FIG. 24, with the electronic level removed.
Figure 29:
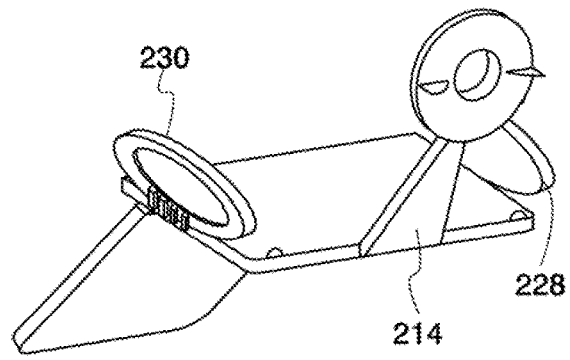
FIG. 29 is a front perspective view of another embodiment of the present invention.

FIGS. 28 and 29 show the device of FIG. 24 with electronic level 210 removed. Keratometer stalk 214 is shown as angled with respect to platform 208 as is handle 206. As seen in FIG. 27, side panels 228, 230 are attached to platform 208 as guards for electronic level 210 when it is attached.

Figure 30:
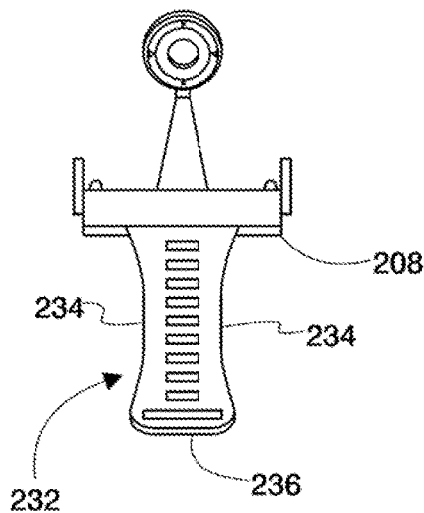
FIG. 30 is a rear view of the device of FIG. 28.

Referring to FIGS. 27 and 30, another embodiment of a handle for the corneal marker is shown. Handle 232 has a shaped contour 234 formed on either side thereof extending from platform 208 to handle end 236. The shaping of handle 234 provides a customized grip that may be preferable to certain users of the device.

Any number of marking blades can be used on any of the keratometers described herein, as desired. Individual marking blades on each of the keratometer assemblies may be inked or not inked to provide a desired number of reference marks on the cornea for surgical purposes.

While electronic levels 166, 210 have been described as providing visual indicators such as LEDs to indicate when the device is level it should be understood that audible signals can be produced as well, with different sounds indicating "left-right-level" attitudes. Thus, a surgeon can determine correct positioning of the corneal marker either visually, audibly, or both.

In another embodiment of the present invention, a more fully featured apparatus is provided for detecting the orientation of a patient's head in one, two or three directions, and in some instances, correlating the measured orientation of the patient's head with a marking instrument.

Figure 31:
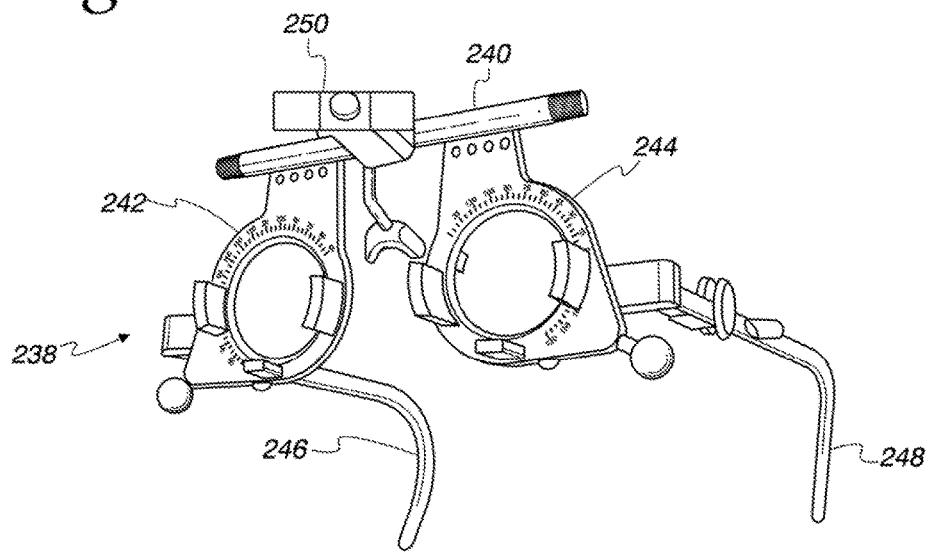
FIG. 31 is a perspective view of another embodiment of the present invention.

Referring now to FIG. 31, the numeral 238 indicates generally a trial frame used by optometrists to perform measurements on a patient's eyes during the process of fitting the patient for glasses.

Frame 238 has a cross-bar 240 to which eyepieces 242, 244 are attached. A pair of temples 246, 248 are attached respectively to eyepieces 242, 244 respectively, allowing a patient to wear trial frame 238 in the same manner as a pair of eyeglasses.

Figure 33:
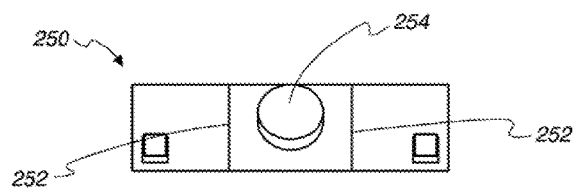
FIG. 33 is a front view of a level used in FIGS. 31 and 32.

In the example shown in FIG. 31, a spirit level 250 is mounted to cross-bar 240 in a manner such that when cross-bar 240 is horizontal the bubble in spirit level 250 will be between the two scribe marks. An enlarged view of spirit level 250 is shown in FIG. 33 with scribe marks 252 and bubble 254.

Figure 32:
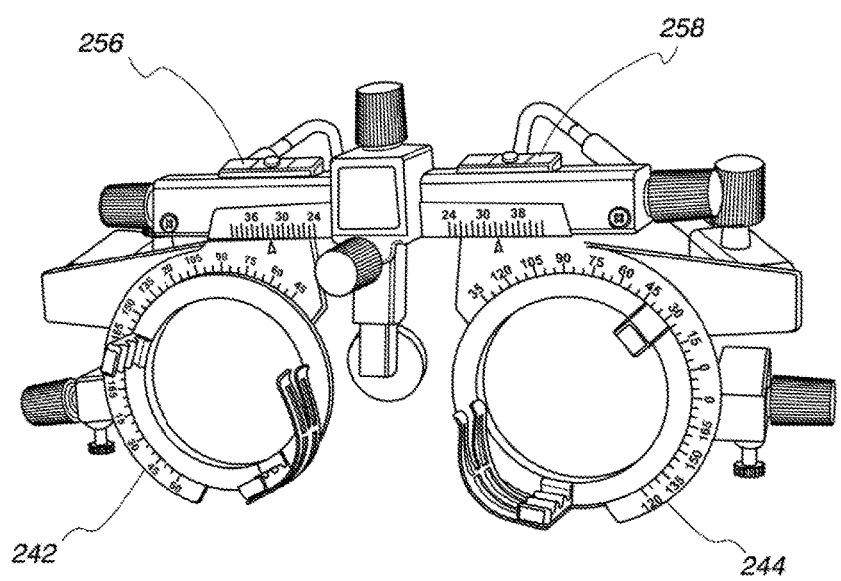
FIG. 32 is a front view of a variation of FIG. 32.

Referring now to FIG. 32, a variation of frame 238 is shown wherein one spirit level 256 is mounted to each eyepiece 242 and 244.

In use, a patient puts on frame 238 as though it were a pair of glasses and, during the patient's examination, the attitude of the patient's head with respect to the horizontal is adjusted by visually viewing spirit levels 250, or 256 and 258. When the patient's head is horizontally level, the steep angle can then be measured more accurately as described hereinabove.

As described above, an electronic level such as 166 or 210 can be substituted for the spirit levels in the foregoing embodiments.

It is possible to measure the orientation of a patient's head in more than one axis or direction. For example, it may be desirable to measure the horizontal inclination of the patient's head as has been discussed heretofore, and also measure the tilt forward or back of the patient's head. Likewise, it may also be desirable to measure the height of the patient's head above a given datum such as the floor or the chair seat in which the patient is seated. To do so would require a leveling device with broader or expanded capabilities.

Figure 34:
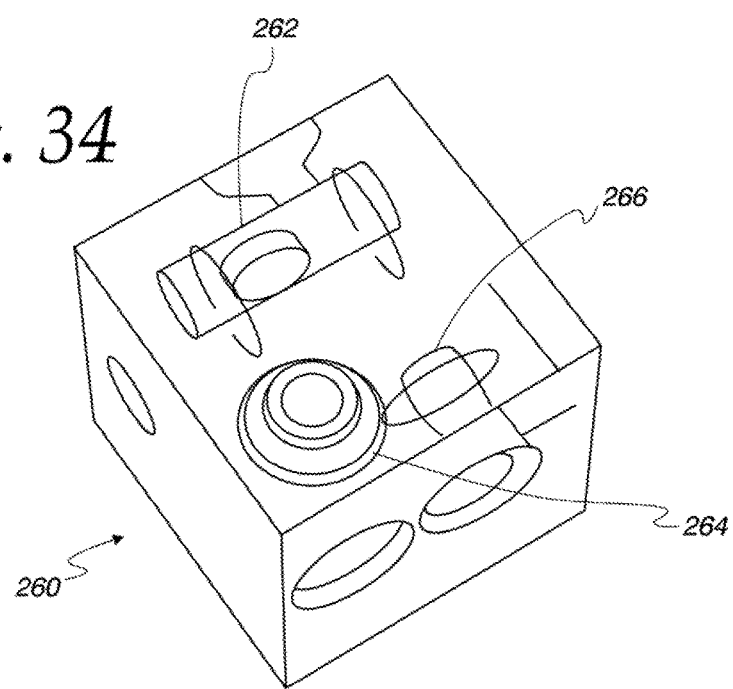
FIG. 34 is a perspective view of a tri-axis spirit level.

Referring now to FIG. 34, a three-axis spirit level 260 is shown as a transparent cube having a first spirit level 262 measuring horizontal adjustment, a second spirit level 264 measuring vertical alignment and a third spirit level measuring horizontal alignment perpendicular to the direction of first level 262. For purposes of description, the axis of horizontal alignment will be referred to as the x-axis, the axis of vertical alignment will be referred to as the y-axis and the remaining axis will be referred to as the z-axis.

Figure 35:
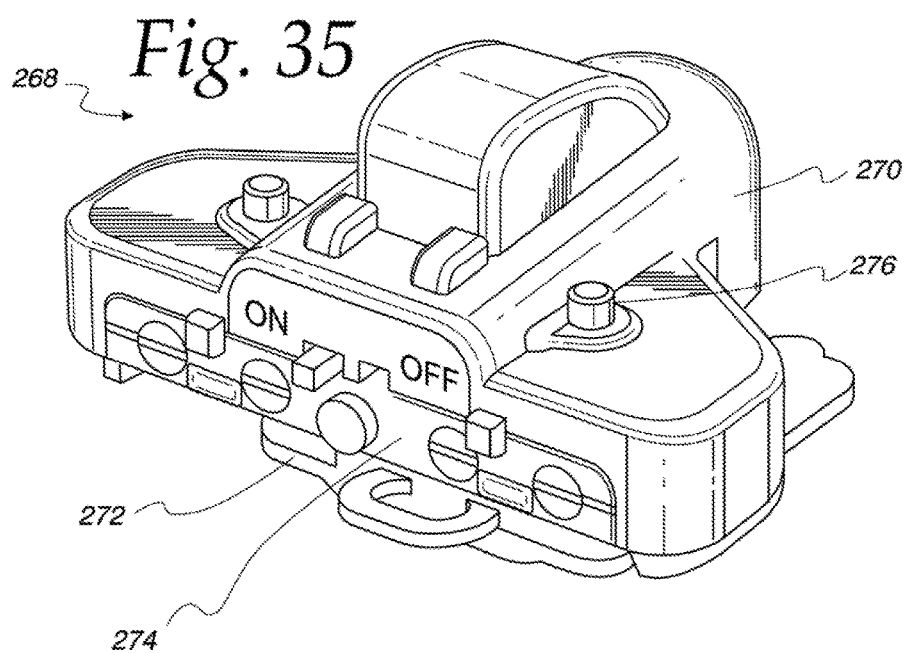
FIG. 35 is a perspective view of a first electronic level indicating device capable of one-, two- or three-axis measurement.

Referring to FIG. 35, the numeral 268 identifies generally an electronic level similar in design and construction to those shown previously as electronic levels 166, 210. Level 268 is modified to be capable of measuring deflection in the x, y and z-axis directions. Level 268 has a housing 270 and a mounting plate 272 allowing attachment of Level 268 to a frame such as those shown in FIGS. 31 and 32. Level 268 has a front facing indicator light array 274 and further has an off-on switch 276.

Figure 36:
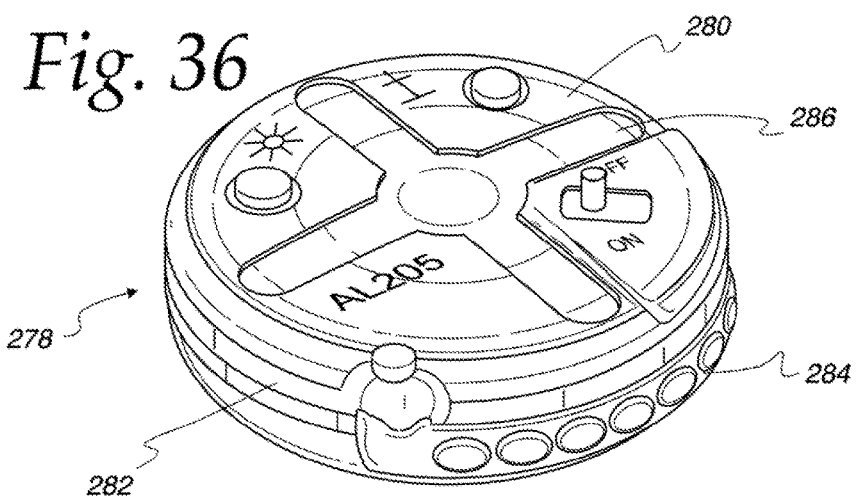
FIG. 36 is a perspective view of a second electronic level indicating device capable of one-, two- or three-axis measurement.

Referring now to FIG. 36 the numeral 278 indicates generally a leveling device having the capability of measuring and detecting deflection in the x, y and z-axis directions. As seen in FIG. 36, leveling device 278 is generally disk shaped having a top surface 280 and a lateral or side surface 282. As seen in FIG. 36, leveling device 278 has a first indicator light array 284 positioned on side wall 282 and a second indicator light array 286 positioned on top surface 280.

Use of leveling devices such as 268 and 278 allows the measurement of a patient's head orientation in one, two or three directions. For the purposes of this description, the x-axis is the measure of the horizontal attitude of the patient's head as described hereinabove. It is possible to construct electronic levels 268 and 278 such that the tilt of the patient's head perpendicular to the frame, that is, in a "nodding" position can be separately detected. For the purposes of this description this will be referred to as the z-axis. The distance of the patient's head may be measured along the y-axis.

Leveling devices 268 and 278 can then correlate this data to a visual or audio signal. For example, indicator light arrays 274, 284 and 286 may be programmed to illuminate in a first selected color or make a first sound when a desired alignment of the patient's head has been reached along the x-axis, a second color or sound when the y-axis measurement reaches a desired value and a third sound or color with respect to measurements along the z-axis.

As an example, an indicator light flashing red can indicate the attitude of the patient's head in the x-axis direction while an indicator light flashing orange can indicate the position of the patient's head in the z-axis direction. It would then be possible for the examining physician to determine in what position the patient's head would be in the x-axis direction and subsequently in the y-axis direction.

It is also contemplated that the signals generated to activate the individually colored lights can be processed through an analog summarizer to produce an indicator or signal that the patient's head is aligned sufficiently in the x-, y-, and/or z-axis directions to meet the physician's criteria for accurate toric marking. The analog summarizer can be a computer program maintained on a computer or computer network with which the generated signals can be transmitted in a wired or wireless manner.

The summarizer can also be programmed onto a computer-readable card such as a CF card or SD card. A card reader can be built into a leveling device such as device 268 and later removed for data processing and storage.

Figure 37:
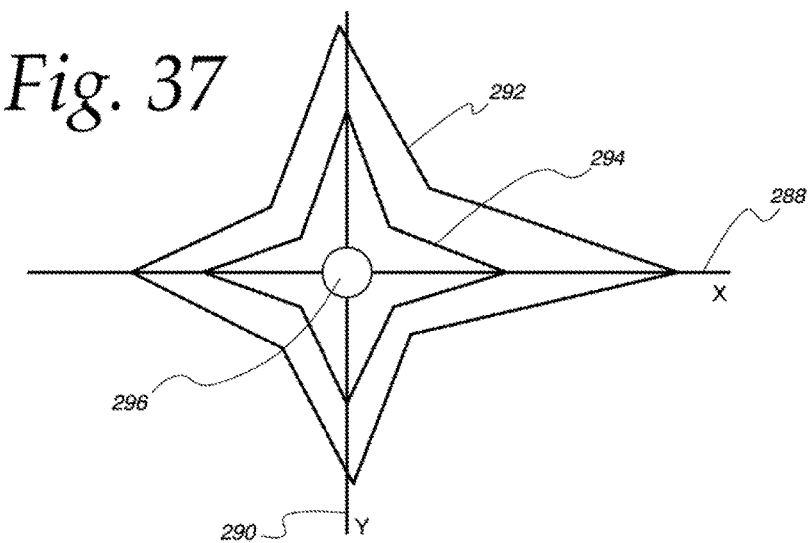
FIG. 37 is a diagram illustrating the operation of the devices of FIGS. 35 and 36.

Referring now to FIG. 37 a diagrammatic representation of this technique is shown. In this example, the x- and y-axes are displayed, with the numeral 288 identifying the x-axis while the numeral 290 identifying the y-axis. Chart line 292 represents a chart of preselected ranges of values within which combined x and y values meet the criteria for activating a red light signal. Chart line 294 identifies a preselected range of values within which combined x and y values meet the criteria for activating an orange light signal. For the purposes of this example, range 294 represents a range of values closer to ideal than range 292. In this example, a red signal calls for further adjustment until an orange signal results. It is also contemplated that a series of different audible tones can also indicate various stages of adjustment.

The numeral 296 indicates a data point at which both the x- and y-axis measured values are ideal. At that point a green light signal is displayed and the physician knows that accurate toric marking can occur. In practice, data point 296 can represent a set of data points that, when achieved, allows marking to be carried out at an acceptable accuracy level.

Figure 38:
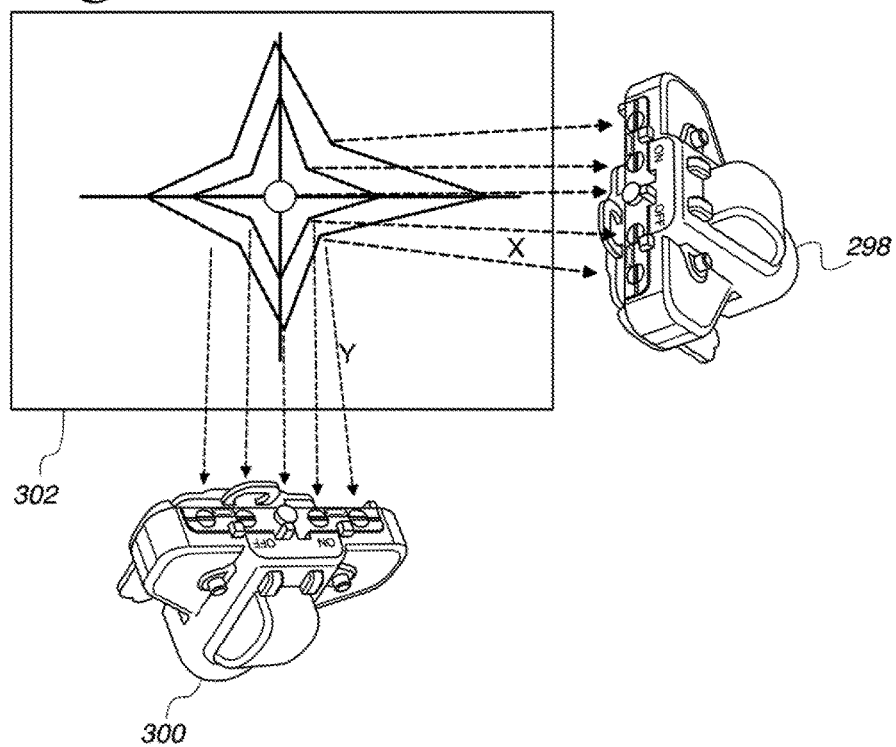
FIG. 38 is a diagrammatic representation of the use of electronic level indicating devices on both a toric marker and a measuring frame.

Use of electronic levels 268 and 278 on both the toric marker and the trial frame can be made in much the same manner as described above in connection with FIG. 10. Referring now to FIG. 38 the numeral 298 identifies generally an electronic level of the type shown in FIG. 35 for mounting to a trial frame such as that shown in FIG. 32, while the numeral 300 identifies a similar electronic level mounted to a toric marker such as that shown in FIG. 11. In this example both electronic levels 298, 300 are selectively capable of measurements in the x-, y- and z-axes.

Signals generated by electronic levels 298 and 300 are transmitted to a signal processor 302 within which analyses are carried out by a signal summarizer programmed to respond by activating a series of visual or aural displays (or both) to inform the physician of the spatial orientation and positioning of each electronic level individually and to compare the values of each to determine when both are in a position within a selected data set to produce an acceptable marking of the patient's eye. As an example, red and orange signals, as described above, with provide cues to positional adjustments while a single green signal can indicate that the physician may proceed with the marking. The signals may be stored as part of the patient's records for later review.

While the foregoing examples have described particular types of frames suitable for use with mechanical or electronic attitude-detecting and measuring devices, such is use is not limited to any specific type of frame. Use of trial frames may be particularly apt because such frames can be used to measure other characteristics of a patient's eye in, for example, an operating room where larger and more conventional apparatus may not be appropriate.

The various types of mechanical and electronic attitude measuring devices uses in the foregoing examples are commonly and commercially available and are readily adaptable to be used to measure in one, two or three axes.

Figure 39:
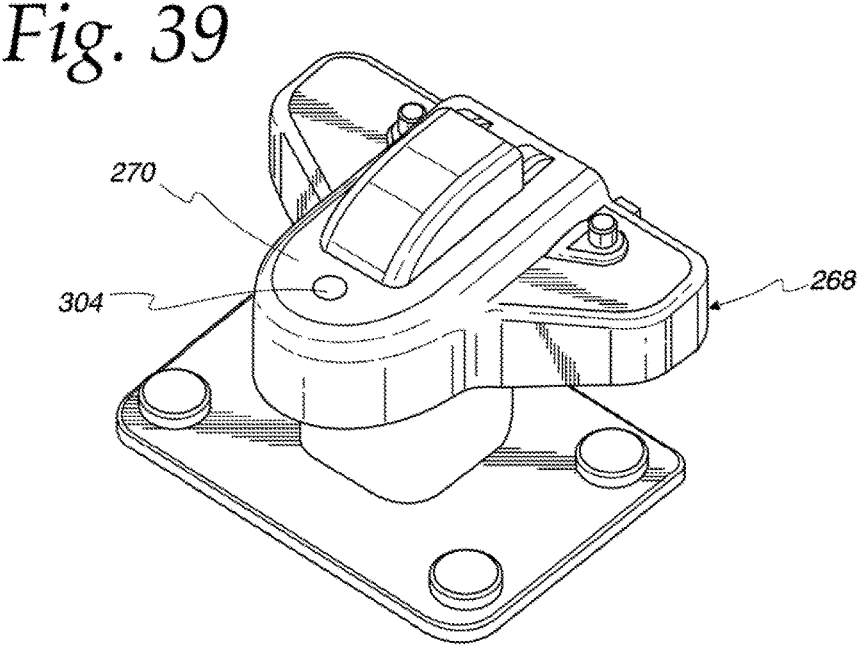
FIG. 39 is a front view of an electronic level having a focusing lamp.

Referring now to FIG. 39, another embodiment of electronic level 268 is seen. Level 268 has a focus lamp 304 set into housing 270. In operation, lamp 304 is activated to blink and the patient is instructed to focus on the light to assure proper alignment of the patient's head for toric measurement.

Figure 40:
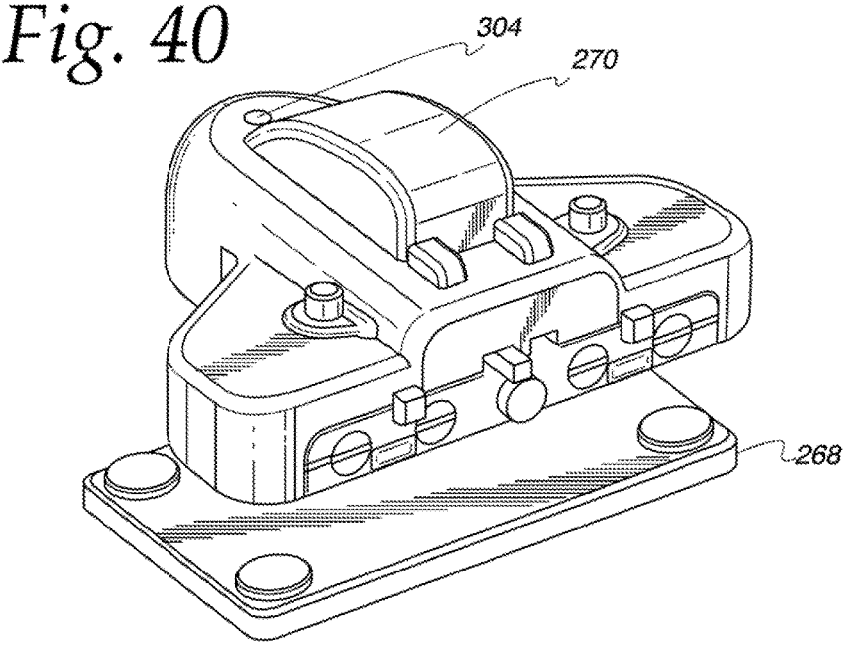
FIG. 40 is a rear view of the level of FIG. 39.

As seen in FIG. 40 the lamp 304 is blocked by housing 270, thus preventing the blinking of lamp 304 from distracting a physician.

What is claimed is:

1. A marking apparatus for marking a cornea of a patient, said marking apparatus comprising:
    a handle having a proximal end and a distal end;
    a mounting platform attached to said handle distal end;
    a tilt detector attached to said mounting platform for detecting a spatial orientation of said marking apparatus with respect to a selected datum, said tilt detector configured to indicate the orientation of said marking apparatus; wherein said tilt detector is an electronic level sensor having at least one light provided thereon to indicate the spatial orientation of said marking apparatus with respect to a selected datum, said electronic level sensor and said at least one light carried on said mounting platform;
    a corneal marker attached to said platform for marking said cornea, said corneal marker configurable to be located at a selected orientation with respect to said selected datum;
    a second tilt detector attachable to a head of the patient for detecting a spatial orientation of the head and the cornea of the patient with respect to said selected datum;
    said second tilt detector configured to indicate the orientation of the head of the patient whereby said first and second tilt detectors are configured to indicate when the orientations of the head of the patient and said corneal marker match with respect to said datum.

2. The marking apparatus as recited in claim 1 wherein at least one of said first and second tilt detectors is an electronic sensor.

3. The marking apparatus as recited in claim 2 wherein said at least one electronic sensor has a visual display configured to produce visual signals as said at least one sensor moves with respect to said datum.

4. The marking apparatus as recited in claim 2 wherein said at least one sensor has an audible signal generator configured to produce characteristic audibly detectable signals as said at least one sensor moves with respect to said datum.

5. The marking apparatus as recited in claim 1 wherein said datum is selected from at least one of an x-axis; a y-axis; and a z-axis.

6. The marking apparatus as recited in claim 5 further comprising:
    a summarizer configured to compare the orientation of said marking apparatus and the orientation of said second tilt detector with respect to said at least one axis to a table of calculated values;
    and said summarizer further configured to generate at least one of an audio and a visual signal when the orientation of said marking apparatus and the orientation of said second tilt detector meet a predetermined threshold with respect to said table of calculated values.

7. The marking he apparatus as recited in claim 6 wherein said summarizer comprises a computer program.

8. The marking apparatus as recited in claim 6 wherein said at least one of an audio and a visual signal varies in response to a comparison of the orientation of said marking apparatus and said second tilt detector to said table of calculated values.

9. A method for marking the cornea of a patient, said method comprising the steps of:
    (a) obtaining the marking apparatus of claim 1;
    (b) attaching the second tilt detector to the patient;
    (c) manipulating said marking apparatus and said second tilt detector until said first and second tilt detectors indicate that the orientations of the head of the patient and said corneal marker are substantially identical; and
    (d) bringing said marking apparatus into contact with the cornea to create a mark on the cornea.

10. The method of claim 9 further including the step of: selecting said datum to be a true horizontal plane.

* * * * *